United States Patent
Hubler et al.

(10) Patent No.: US 8,338,395 B2
(45) Date of Patent: Dec. 25, 2012

(54) METHODS AND PHARMACEUTICAL COMPOSITIONS FOR RELIABLE ACHIEVEMENT OF ACCEPTABLE SERUM TESTOSTERONE LEVELS

(75) Inventors: Doris Hubler, Jena (DE); Sabine Fricke, Jena (DE); Jan-Peter Ingwersen, Berlin (DE); Wilheim Kuhnz, Berlin (DE)

(73) Assignee: Bayer Intellectual Property GmbH, Monheim (DE)

( * ) Notice: Subject to any disclaimer, the term of this patent is extended or adjusted under 35 U.S.C. 154(b) by 717 days.

(21) Appl. No.: 12/391,655

(22) Filed: Feb. 24, 2009

(65) Prior Publication Data

US 2009/0156564 A1    Jun. 18, 2009

Related U.S. Application Data

(62) Division of application No. 10/798,780, filed on Mar. 12, 2004, now Pat. No. 7,718,640.

(60) Provisional application No. 60/454,312, filed on Mar. 14, 2003.

(51) Int. Cl.
   *A61K 31/56* (2006.01)
(52) U.S. Cl. ........................ 514/170; 514/182
(58) Field of Classification Search .................. 514/170, 514/182
   See application file for complete search history.

(56) References Cited

U.S. PATENT DOCUMENTS

| | | | |
|---|---|---|---|
| 3,164,520 A * | 1/1965 | Huber | ........................ 514/174 |
| 4,181,721 A | 1/1980 | Speck et al. | |
| 4,212,863 A | 7/1980 | Cornelius | |
| 5,364,632 A | 11/1994 | Benita et al. | |
| 6,274,582 B1 | 8/2001 | Marin | |

FOREIGN PATENT DOCUMENTS

| | | |
|---|---|---|
| DE | 25 48 413 | 4/1977 |
| EP | 0 001 851 A1 | 5/1976 |
| EP | 1 313 511 | 11/2005 |
| GB | 1 567 515 A1 | 5/1980 |
| GB | 1 569 286 | 6/1980 |
| WF | WO 97/40823 | 11/1997 |
| WO | WO 95/12383 | 5/1995 |
| WO | WO 95/18603 | 7/1995 |
| WO | WO 98/36770 | 8/1998 |
| WO | WO 99/67270 | 12/1999 |
| WO | WO 99/67271 | 12/1999 |
| WO | WO 00/59512 | 10/2000 |

OTHER PUBLICATIONS

Database WPI, Section Ch, Week 199524, Derwent Publications Ltd. London, GB, AN 1995-185577 XP002264337, 1995.

Wang Lie-zhen, Wang et al., The Therapeutic Effect of Domestically Produced Testosterone Undecanoate in Klinefelt Syndrome (Abstract), 1991.

Zhao-dian, Chen et al., "Clinical Study of Testosterone Undecanoat Compound on Male Contraception", First Affiliated Hospital of Zhejiang Medical University, (Abstract), 1993.

(Continued)

*Primary Examiner* — San-Ming Hui
(74) *Attorney, Agent, or Firm* — Millen, White, Zelano & Branigan, P.C.

(57) ABSTRACT

Described are methods for providing prolonged physiologically acceptable steady state serum testosterone levels in a patient deficient in endogenous testosterone levels, methods for male contraception and methods for treating a disease or symptom associated with deficient endogenous levels of testosterone in a man, by intramuscularly administering testosterone esters in a vehicle.

27 Claims, 1 Drawing Sheet

OTHER PUBLICATIONS

Zhang, Gui-Yuan, et al., "A Clinical Trial of Injectable Testosterone Undecanoate as a Potential Male Contraceptive in Normal Chinese Men*", The Journal of Clinical Endocrinology & Metabolism (1999).

Zhang, Gui-Yuan, et al., "A Pharmacokinetic Study of Injectable Testosterone Undecanoate in Hypogonadal Men", Journal of Andrology, vol. 19, No. 6, Nov./Dec. 1998, pp. 761-768.

Behre, H.M. et al., "Intramuscular Injection of Testosterone Undecanoate for the Treatment of Male Hypogonadism: Phase I Studies", European Journal of Endocrinology, 140, pp. 414-419, (1999).

Von Eckardstein, Sigrid, et al. "Treatment of Male Hypogonadism with Testoterone Undecanoate Injected at Extended Intervals of 12 Weeks: A Phase II Study", Journal of Andrology, vol. 23, No. 3, May/Jun. 2002.

Incomplete Search Report dated Dec. 10, 2003.

European Search Report dated May 28, 2004.

International Search Report dated Dec. 9, 2004.

"Le Manuel Merck De Diagnostic Et Therapeutique", Merck Res. Labs., 1999, pp. 2352-2356, XP-002305717.

"Male Hypogonadism" The Merck Manual, Sec. 19, Ch. 269, Endocrine and Metabolic Disorders, 2005.

International Preliminary Report on Patentability for PCT/IB2004/000716, 2004.

E. Nieschlag, et al. "Repeated intramuscular injections of testosterone undecanoate for substitution therapy in hypogonadal men", Blackwell Science Ltd., 1999, pp. 757-763.

Abshagen, K. et al., Expl. Klink, Endocrinol. Deab. 105, Supp. 1, p. 21, 1997.

Rifkin, C. et al., J. Pharm. Sci. 53, 891, 1964.

Christoph, A. et al., The Aging Male, Supp. 1:54, Abstract 107, 2000.

Christoph, A. et al., "Endocrinology & Diabetes", Supp. 1, Vo. 108, S. 177, pFR176, 2000.

Partsch, C. J. et al., "Eur. J. Endocrinol.", 132:514-19, 1995.

Von Eckardstein, S. et al., "Experim. Clin. Endocrinol. Diab.", 108, Supp. 1, vol. 108, s 178, pFR 183, 2000.

ROC (Taiwan) Search Report dated Feb. 6, 2007.

Schuber, M. et al., Exp. Clin. Endocrinol Diab., Supp. 1, s.62-63, p059, 1999.

* cited by examiner

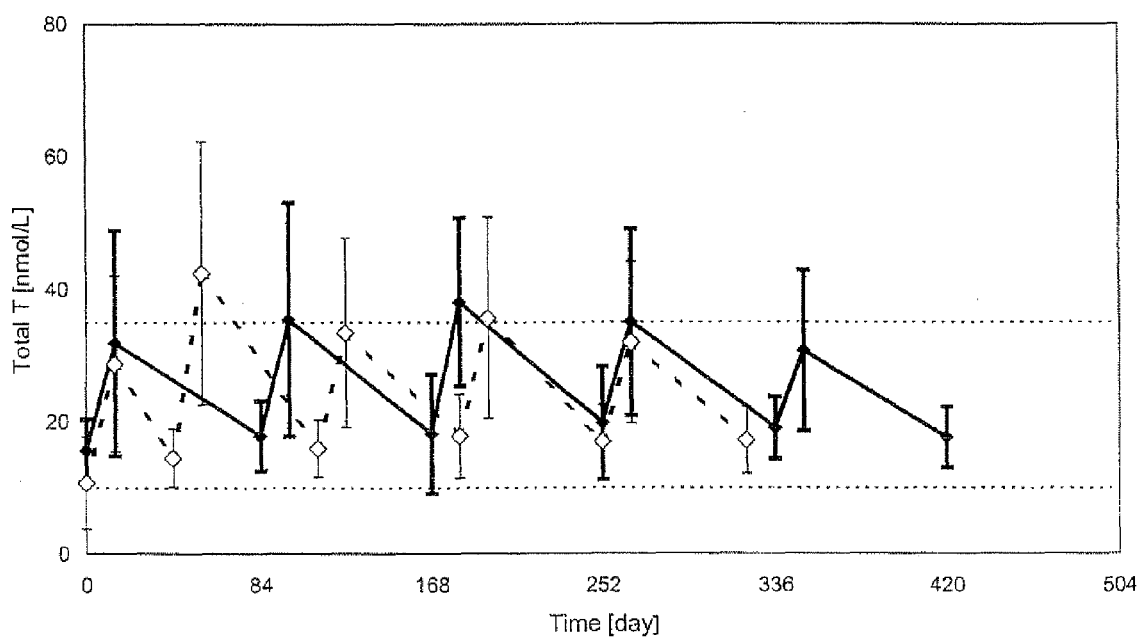

METHODS AND PHARMACEUTICAL COMPOSITIONS FOR RELIABLE ACHIEVEMENT OF ACCEPTABLE SERUM TESTOSTERONE LEVELS

This application is a divisional of U.S. Ser. No. 10/798,780, filed Mar. 12, 2004 now U.S. Pat. No. 7,718,640. This application claims priority benefit of U.S. Provisional Application Ser. No. 60/454,312, filed Mar. 14, 2003. The entire disclosures of all applications, patents and publications cited herein, including the corresponding U.S. Ser. No. 10/798,780 and U.S. Provisional Application Ser. No. 60/454,312, are incorporated by reference herein.

FIELD OF INVENTION

The present invention relates to the field of pharmaceutical formulation science as well as the field of therapeutic applications of hormones in hormone replacement therapy in men and in male contraception. In particular, the invention relates to compositions of testosterone esters in castor oil that upon intramuscular injection provides reliable physiological acceptable serum testosterone levels for a prolonged period.

BACKGROUND

For several decades, testosterone preparations have been used clinically to treat primary and secondary male hypogonadism in order to achieve normal physiologic levels of testosterone and to relieve symptoms of androgen deficiency. Furthermore, testosterone preparations have been used in male contraception as the sole active therapeutic agent for suppressing spermatogenesis or as an active agent in combination with progestins or further gonadotropin suppressive agents.

Male hypogonadism is characterised by a deficiency of endogenous testosterone production resulting in abnormally low levels of circulating testosterone, i.e. serum testosterone levels below 10 nmol/l.

Male hypogonadism may be classified in primary and secondary causes: primary or hypergonadotropic hypogonadism, congenital or acquired, may be derived from testicular failure due to cryptorchidism, bilateral testicular torsion, orchitis, orchidectomy, Klinefelter syndrome, chemotherapy or toxic damage from alcohol or heavy metals.

Secondary or hypogonadotropic hypogonadism, congenital or acquired, is caused by idiopathic gonadotropin releasing hormone (GnRH) deficiency or pituitary-hypothalamic injury from tumours, trauma, or radiation. In the vast majority of cases, hypogonadism is related to a primary defect of the testes.

The clinical picture of hypogonadal adult men varies a lot. For example, testosterone deficiency is accompanied by symptoms of different severity, including sexual dysfunction, reduced muscle mass and muscle strength, depressed mood and osteoporosis.

Current standard therapies aims at restoring physiologically relevant levels of testosterone in serum, which applies to concentrations of about 12 nmol to about 36 nmol. Intramuscular injection of testosterone esters, such as testosterone enanthate or testosterone cypionate, administered every two to three weeks, still represents the standard of testosterone replacement therapy in most countries of the world. Apart from the inconvenience of frequent visits to the doctor's office, the patients complain about variations in well-being due to short-term fluctuations of serum testosterone levels resulting from the pharmacokinetic profile after intramuscular injection of for example testosterone enanthate.

Recently, the use of testosterone esters with longer aliphatic chain length and/or higher hydrophobicity, such as testosterone undecanoate, has become interesting in terms of prolonging the interval between injections. Longer intervals between injections are advantageous from a patient's point of view.

For example Zhang G et al, 1998, report the injection of compositions comprising testosterone undecanoate in a concentration of 250 mg in 2 ml tea seed oil so as to administer a dose of 500 mg or 1000 mg of testosterone undecanoate (Zhang G et al., *A pharmacokinetic study of injectable testosterone undecanoate in hypogonadal men. J Andrology*, vol 19, No 6, 1998). Zhang et al, 1999, relates to injectable testosterone undecanoate as a potential male contraceptive (Zhang et al, *J clin Endocrin & metabolism*, 1999, vol 84, no 10, p 3642-3646).

Furthermore, Behre et al, 1999, relates to testosterone undecanoate preparations for testosterone replacement therapy such as testosterone undecanoate 125 mg/ml in tea-seed oil and testosterone undecanoate 250 mg/ml in castor oil (Behre et al, *Intramuscular injection of testosterone undecanoate for the treatment of male hypogonadism: phase I studies. European J endocrin*, 1999, 140, p 414-419).

Intramuscular injections of 250 mg testosterone undecanoate and 200 mg MPA every month have been suggested for male contraception (Chen Zhao-dian et al, *clinical study of testosterone undecanoate compound on male contraception. J Clin androl*, 1986, vol 1, issue 1, abstract)

Wang Lie-zhen et al. report testosterone replacement therapy using monthly intramuscular injections of 250 mg testosterone undecanoate (Wang Lie-zhen et al. *The therapeutic effect of domestically produced testosterone undecanoate in Klinefelt syndrome*. New Drugs Market 8: 28-32, 1991.

WO 95/12383 (Chinese application) relates to injectable compositions of testosterone undecanoate in vegetable oils, optionally in admixture with benzyl benzoate. The compositions are injected monthly when applied for male contraception and substitution therapy.

U.S. Pat. No. 4,212,863 is a patent which relates to a lipid formulation of steroids for oral or parenteral administration various oil carriers, optionally including benzyl benzoate, which is said to lower the viscosity of the lipid carrier and/or enhance the solubility.

Eckardstein and Niesclag, 2002, report the treatment of hypogonadal men with testosterone undecanoate, wherein physiological relevant levels of testosterone may be achieved for an extended period of time upon initially injecting testosterone undecanoate four times in intervals of 6-weeks followed by subsequent injections of longer intervals (Eckardstein and Niesclag, *treatment of male hypogonadism with testosterone undecanoate injected at extended intervals of 12 weeks, J Andrology*, vol 23, no 3, 2002)

However, it is well known that therapies with testosterone esters, such as testosterone undecanoate, still need to be improved in terms of achieving reliable serum testosterone levels in the physiologically acceptable range for a prolonged period of time. There is a need of providing reliable standard regimens acceptable for a broad population of men in need thereof, preferably regimens without the need of occasional control of serum testosterone levels, and regimens wherein steady state conditions are achieved within a shorter time period.

SUMMARY OF INVENTION

The present invention relates to injectable compositions comprising long-term acting testosterone esters for use in testosterone replacement therapy. Upon injecting the compositions, physiologically normal levels of testosterone in serum are reached within a short time period. Furthermore, the physiologically normal serum levels of testosterone are maintained for an extended period of time, without showing fluctuations in the hypogonadal range. The compositions are chemically stable with respect to the testosterone ester as well as physically stable with respect to the vehicle for a prolonged time.

Therefore, in a first aspect the present invention relates to a composition intended for injectable administration, such as by intramuscular injections, the composition comprises a testosterone ester selected from the group of esters consisting of linear and branched C-9 to C-16 alkanoates, preferably testosterone undecanoate; and a vehicle, which comprises castor oil and a co-solvent.

Furthermore, in a second aspect the invention relates to a method of treating diseases and symptoms associated with deficient endogenous levels of testosterone in a man. For example methods of treating primary and secondary hypogonadism; hypophyseal diseases; symptoms of sexual dysfunction; symptoms of reduced muscle mass and muscle strength; symptoms of depressed mood; or symptoms of osteoporosis. The method comprises administering by injection a testosterone ester selected from the group of esters consisting of linear and branched C-9 to C-16 alkanoates, such as testosterone undecanoate, according to a particular scheme comprising:
i) an initial phase of 2 to 4 injecting a dose of said testosterone ester with an interval of 4 to 8 weeks between each administration, each dose is in an amount therapeutically equivalent to a dose of testosterone undecanoate of between 500 mg and 2000 mg; followed by
ii) a maintenance phase of subsequent injecting a dose of said testosterone ester with an interval of at least 9 weeks between each subsequent administration, each dose is in an amount therapeutically equivalent to a dose of testosterone undecanoate of between 500 mg and 2000 mg.

Further aspects relate to the use of the above-mentioned compositions for male contraception.

Still further aspects relate to the use of a testosterone ester selected from the group of esters consisting of linear and branched C-9 to C-16 alkanoates for the preparation of medicaments that are in a form for parenteral administration, such as in a form for intramuscular injection and further comprises a vehicle comprising castor oil and a co-solvent. The medicaments in question are primarily for treating primary and secondary hypogonadism in a male for treating diseases and symptoms associated with deficient levels of testosterone in a male who are in therapy with a progestin or a further gonadotropin suppressive agent.

DETAILED DESCRIPTION OF THE INVENTION

The present inventors provide, herein, standard methods resulting in superior pharmacokinetic profiles of testosterone in vivo. Physiologically normal serum levels of testosterone are achieved quickly after initiating the therapy with the testosterone preparations of the invention and reliable testosterone serum levels within the normal physiological range is maintained for an extended period of time. Advantageously, the standard methods reported herein, allows for significant prolonged intervals between injections, and the serum testosterone levels may not necessarily need to be controlled.

According to the invention, the standard method includes combining the suitable formulation of a composition comprising slowly degradable testosterone esters, such as testosterone undecanoate, and suitable injection schemes of well defined doses of such testosterone esters.

Without being adapted to a particular theory, a number of parameters will influence the pharmacokinetic profile of a testosterone ester that is injected intramuscularly, in particularly if a depot effect is desirable. A depot effect can in general be achieved by selecting a testosterone ester that slowly degrades into free testosterone once it has entered the blood circulation. An additional factor contributing to the depot effect is the diffusion rate of the testosterone ester from the site of injection to the circulating blood system. The diffusion rate may depend on the dose and the volume injected in that the concentration gradient of the testosterone ester at the site of administration is thought to affect the diffusion rate. Furthermore, the type of vehicle injected together with the testosterone esters will influence the rate of diffusion of testosterone esters from the vehicle into the surrounding tissues and the rate of absorption into the blood circulation. Therefore, the partition coefficient (n-octanol-water partition coefficient) of the testosterone ester in the vehicle as well as the viscosity of the vehicle should be considered in order for adapting a depot effect following intramuscular injection of testosterone esters.

Moreover, for safety reasons and ease of handling, the testosterone ester should be proper dissolved in a vehicle. Often it is impossible to predict which kind of vehicles that both can dissolve the testosterone ester and provide the needed depot effect. Therefore, mixtures of various solvents may be required, although undesirable from a manufacturing point of view.

The present inventors have recognised that an effective depot effect in vivo of testosterone esters, such as testosterone undecanoate, is achieved when injecting the testosterone esters intramuscularly in a vehicle comprising castor oil and a suitable co-solvent. The co-solvent may lower the viscosity of the castor oil and then solve the problem with high viscosity of the castor oil when being injected. On the other hand, the co-solvent may increase the diffusion rate of the testosterone ester, resulting in a lower depot effect following intramuscular injection.

As may be understood, a first aspect of the invention relates to a composition comprising a testosterone ester selected from the group of esters consisting of linear and branched C-9 to C-16 alkanoates; and a vehicle comprising castor oil and a co-solvent.

The composition is formulated for parenteral administration, preferably intramuscular injection.

The term "linear and branched C-9 to C-16 alkanoates" is denoted to mean aliphatic esters with chain lengths from 9 to 16 carbon atoms. That is to say that the aliphatic esters are made of 9 to 16 carbon atoms. Thus, in suitable embodiments of the invention, the testosterone ester is selected from esters, wherein the ester group is a noncanoate, a decanoate, an undecanoate, a dodecanoate, a tridecanoate, a tetradecanoate, a pentadecanoates, or a hexadecanoate. Preferably, the ester group may be placed in the 17β-position of the testosterone molecule. In a presently interesting embodiment, the testosterone ester is testosterone undecanoate, a testosterone ester with an aliphatic side chain in 17β position. The chemical name is 17β-hydroxyandrost-4-en-3-one undecanoate.

The term "castor oil" is meant to encompass castor oil refined for parenteral use, for example as described in DAB, wherein the castor oil is provided in a form without antioxidants and obtained with the first pressure of *ricinus communis* without using extraction processes. It should also be understood that the castor oil are not hydrogenated or at least in part not hydrogenated. In some embodiments, a minor part of the double bonds may be hydrogenated, For example, less than 20% w/w of the double bonds may be hydrogenated. Preferably less than 10% w/w of the double bonds may be hydrogenated, more preferably less than 5% w/w, even more preferably less than 2% w/w, most preferably less than 1% w/w of the double bonds are hydrogenated. Castor oil appears as a liquid at room temperature.

As stated, the co-solvent of the vehicle is, at least in part, an essential element of the compositions of the invention. Such co-solvents may in general be defined by its capability of reducing the viscosity of castor oil, as determined by a Höppler viscosimeter.

Injection of high viscous vehicles, such as castor oil, is associated with technical limitations to the size of cannula due to the resistance of the vehicle when passing the cannula. It is commonly recommended that the viscosity of an injection solution should be kept below 100 mPas. In certain instances, the viscosity of a final product, ready to be injected, such as a re-constituted product may be, e.g., less than 100 mPas, such as 90 mPas, 80 mPas, 70 mPas at room temperature. In some embodiments, the viscosity of the vehicle is less than 60 mPas, 50 mPas, 40 mPas or 30 mPas at room temperature.

Thus, suitable embodiments of the invention relate to those wherein the co-solvent is selected from those that when being mixed with castor oil in an oil:co-solvent volume ratio of between 1:0.2 to 1:3, the viscosity drops from 950-1100 mPas to 20 mPas at room temperature. Preferably, the co-solvent is selected from those, wherein the viscosity drops from 950-1100 mPas to about 80-100 mPas, when the co-solvent is being mixed with castor oil in an oil:co-solvent volume ratio of about 1:1 to 1:3. The viscosity of the vehicle may be determined with a Höppler type viscometer. The Höppler type viscometer consists of an inclined glass tube inside which a sphere with known density, mass and diameter glides through the liquid to be measured, and the falling time of the ball is measured. The viscosity is measured at a fixed temperature, often room temperature such as 20° C. or 25° C. The measurements are repeated until the values are constant.

The co-solvent may be characterised by is ability to reduce the viscosity of a vehicle, such as castor oil, of the solvent in a ratio dependent manner.

In one interesting embodiment of the invention the viscosity of a mixture of castor oil and a co-solvent in a volume ratio of 1:0.1 to 1:1.7 is reduced from 60% to 5% to that of castor oil.

In a suitable embodiment of the invention, the viscosity of a mixture of castor oil and a co-solvent in a ratio of 1:0.02 by volume is reduced by about 10% relatively to the viscosity of castor oil. In other various embodiments, when the ratio between the oil and co-solvent is of 1:0.04 by volume the viscosity is reduced by 20% relatively to the viscosity of castor oil, when the ratio is of 1:0.08 by volume the viscosity is reduced by 25%, when the ratio is of 1:0.1 by volume the viscosity is reduced by 40%, when the ratio is of 1:0.2 by volume the viscosity is reduced by 50%, when the ratio is 1:0.35 by volume the viscosity is reduced by 75%, when the ratio is of 1:0.5 by volume the viscosity is reduced by 80%, when the ratio is of 1:1 by volume the viscosity is reduced by 90%, or when the ratio is 1:1.6 by volume the viscosity is reduced by 95%.

In further interesting embodiments, the viscosity of the composition is below 100 mPas. Furthermore, in some embodiments the viscosity of vehicle, such as the mixture of castor oil and a co-solvent, such as benzyl benzoate is below 90 mPas, the viscosity of the vehicle is about 60-100 mPas, such as 70 to 100 mPas, such as 80-90 mPas at room temperature (20° C. to 25° C.).

As mentioned, the viscosity of the injected vehicle may determine the pharmacokinetic profile of an injected substance. Thus, in order to obtain a final product with a suitable depot effect in vivo, the castor oil and co-solvent is in a volume ratio ranging between 1:0.2 to 1:3, such as between 1:0.5 to 1:3, or between 1:0.75 to 1:2.5. Preferably, the volume ratio is in the range from 1:1 to 1:2.

In presently interesting embodiments of the invention, the co-solvent is benzyl benzoate. In principle, other types of co-solvents may be applicable for use in combination with castor oil, such as for example ethanol or benzyl alcohol. Interesting co-solvents of the present invention are those which are capable of dissolving the testosterone esters and is miscible with castor oil. Of special interest are co-solvents suitable for dissolving about 100-500 mg, such as 250 mg of testosterone undecanoate in 1 mL of the co-solvent within 50 minutes at 40° C. or within 20 minutes at 60° C.

The solubility of the testosterone esters may be affected upon adding a co-solvent to the castor oil vehicle. Probably the solubility may be improved. Thus, in some embodiments, the testosterone ester is completely dissolved in the composition, and in other embodiments the testosterone ester is partly dispersed in the composition. Preferably, the testosterone esters are fully dissolved in the vehicle. That is to say that no particles of testosterone may be detected by X-ray diffraction analysis.

The present invention provides compositions, wherein the co-solvent is present in the vehicle at concentrations ranging from 10 to 90 vol %. Preferably, the concentration of the co-solvent in the vehicle ranges between 15 to 85 vol %, more preferably between 20 to 80 vol %, such as between 45 to 85 vol % or 55 to 85 vol %.

In other words, the vehicle comprises the castor oil in a volume concentration ranging between 20 to 85 vol %. Preferably, the concentration of castor oil in the vehicle ranges between 25 to 60 vol %, such as between 25 to 55 vol %. In preferred embodiments of the invention, the concentration of castor oil in the vehicle ranges between 25 to 50 vol %, such as between 25 to 45 vol % or 25 to 40 vol %.

It should be understood that intentionally the composition should not comprise another plant oil, such as for example tea seed oil. That is to say that castor oil is the only plant oil present in the composition or that castor oil makes up at least 50% by volume of the total content of the plant oil in the vehicle, such as at least 60%, 70%, 80% or 90% by volume.

It is generally considered that the needed concentration of the co-solvent depends on a number of factors, such as i) the amount of testosterone ester in the injection vehicle, ii) the required reduction of viscosity and iii) the release properties of the injection vehicle with respect to the testosterone ester at the site of injection (diffusion rate). In interesting embodiments of the invention, the co-solvent makes up at least 10 vol % of the vehicle, preferably at least 15 vol %, more preferably of at least 25 vol %, most preferably at least 40 vol %, such as at least 50 vol %. Interestingly, the co-solvent is in an amount ranging from about 40 to 80 vol % of the vehicle, such as about 50 to 70 vol %, most preferably the co-solvent is in an amount ranging from about 55 to 65 vol % of the vehicle.

In some embodiments of the invention, the concentration of the co-solvent in the vehicle should be limited in order to reduce the diffusion rate of the testosterone esters, for instance at the site of injection. Therefore in some embodiments the concentration of co-solvent in the vehicle should be less than 90 vol %, preferably less than 85 vol %, more preferably less than 80 vol %, such as less than 75 vol %.

The volume that can be injected intramuscularly is known to affect the release rate of an active principle from a vehicle. An injection volume of 5 mL is generally considered as the maximum volume that can be administrated by one single intramuscular injection to one injection site. When intramuscular injection of volumes greater than 5 mL is required, the injection volume needs to be divided into two or more separate injections to different injection sites. However, multiple injections for the administering of one dose are generally not preferred because of the inconvenience conferred to the patient.

The injection of a single dose to one injection site offers great advantages in controlling the release rate of an active principle, rather than multiple injection of divided single doses. The present invention relates to injection schemes wherein a single dose of a testosterone ester is divided into no more than two separate injections to one or more injection sites. Most preferable, a single dose of a testosterone ester is injected as one single injection to one injection site. Therefore, in presently interesting embodiments of the invention the dose of the testosterone esters is administered as a single injection to one injection site, wherein the injected volume is of 1 to 5 mL, preferably of 1 to 4 mL, such as of 1.5 to 4 mL. Suitable injection volumes of the invention for ensuring reproducible administration volumes and uniform release of the testosterone esters is lower than 5 mL, such as about 5 mL, about 4 mL, about 3 mL, about 2 mL and about 1 mL.

In order for using single injections and low injections volumes, the concentration of the testosterone esters in the compositions need to be relatively high. Thus, a testosterone ester, such as testosterone undecanoate is in a concentration of 100 mg to 1000 mg per mL of the vehicle. In still interesting embodiments, the testosterone ester, such as testosterone undecanoate, is in a concentration of 130 to 750 mg per mL of the vehicle, more preferably of 150 to 500 mg per mL, most preferably of 175 to 400 mg per mL, such as about 250 mg/mL of the vehicle.

The composition may be suitable formulated as a unit dose form such as a unit dose intended for being injected as one single dose. In such embodiments, the testosterone ester, such as testosterone undecanoate, is in a dose of 500 to 4000 mg, preferably of 500 mg to 3000 mg, more preferably of 750 mg to 2000 mg, most preferably of 750 mg to 1500 mg, such as 1000 mg.

It is further contemplated that compositions of the invention comprise a further therapeutically active agent, such as a progestin and/or a further gonadotropin suppressive agent other than a testosterone ester.

As used herein, the term "progestin" encompasses all compounds with progestinic activity such as cyproterone, drospirenone, etonogestrel, desogestrel, gestodene, levonorgestrel, norethisterones, norgestimate, norethindrone, norethindrone acetate, norethynodrel, norgestimate, norgestrel, medrogestone, medroxyprogesterone acetate and progesterone.

The compositions of the invention are chemically stable with respect to the testosterone esters. That is to say that degradation products could not be detected after long term storage (such as after 7 weeks or 17 weeks or even longer) at conditions normally known to accelerate degradation processes, such as variations in temperatures, high and low temperatures and various relative humidity. For example, less than 1% by weight of degradation products of testosterone esters is present after storage of the composition for at least 7 weeks, such as for 16 or 17 weeks, for 6 months, or for 9 or 12 months at 40° C. and 25% RH in darkness. Preferably, less than 0.5% w/w, such as less than 0.2% w/w of degradation products of testosterone esters is present after storage at the above-mentioned conditions.

Moreover, the vehicle comprising castor oil and benzyl benzoate is also highly stable in that no sublimate of the solution is seen upon storage of the composition for a long time at various temperatures.

Compositions according to the invention may be prepared according to techniques known by the skilled person.

A first step in the preparation of a composition of the invention comprises dissolving the testosterone ester in the co-solvent. Then, the testosterone undecanoate/co-solvent solution is combined with castor oil. The final solution may then be filtrated through a 0.2 µm filter, optionally filled into, for instance, amber-glass bottles, before finally sterilised at 180° C. for 3 hours.

It is submitted that the vehicle, wherein the testosterone ester is dissolved, may further comprise one or more excipients, such as preservatives, stabilising agents, other cosolvents and antioxidants. Suitable vehicles are sterile, pyrogen-free and free of particles.

As stated supra, the present inventors have provided a formulation of testosterone esters possessing superior pharmacokinetic profiles of testosterone in the blood upon
- selecting a proper injection vehicle for the testosterone esters so as to ensure slowly diffusion of the testosterone esters from the site of injection and slowly disintegration of the testosterone ester into free testosterone in the blood and
- selecting a simple and reliable administration scheme of such compositions for treating diseases and symptoms associated with deficient endogenous levels of testosterone in a man.

Thus, a further aspect of the invention relates to a method of treating diseases and symptoms associated with deficient endogenous levels of testosterone in a male, such as a mammalian male, such as a man, comprising administering by injection, such as by intramuscular injection, a testosterone ester selected from the group of esters consisting of linear and branched C-9 to C-16 alkanoates, the method further comprises;
i) an initial phase comprising 2 to 4 injections of a single dose of said testosterone ester with an interval of 4 to 10 weeks between each injections, each dose is in an amount therapeutically equivalent to a dose of testosterone undecanoate of between 500 mg and 2000 mg; followed by
ii) a maintenance phase comprising subsequent injections of a single dose of said testosterone ester with an interval of at least 9 weeks between each subsequent injection, each dose is in an amount therapeutically equivalent to a dose of testosterone undecanoate of between 500 mg and 2000 mg.

The phrase "therapeutically equivalent" is meant to define the dose of any testosterone ester of the invention in terms of the therapeutically relevant dose of testosterone undecanoate. For example, if it has been shown that the therapeutically relevant dose of testosterone undecanoate for re-instating testosterone blood levels in the range of 12-35 nmol is about 1000 mg, the dose of any testosterone ester of the invention is the dose achieving the same effect as testosterone undecanoate.

The term "administration by injection" is meant to encompass any form for injection into a muscle or subcutaneous injection. The preferred form of injection is by intramuscular injection.

Preferably, the initial phase comprises 2 or 3 injections of a dose of said testosterone ester, such as testosterone undecanoate, with an interval of 4 to 8 weeks between each injection. In a most interesting embodiment, the initial phase includes 2 injections of a single dose of said testosterone ester with an interval of 4 to 10 weeks between each injection. In currently interesting embodiments, the interval between injections in the initial phase is 6 weeks.

In further aspects, the invention relates to the use of a testosterone ester selected from the group of esters consisting of linear and branched C-9 to C-16 alkanoates for the preparation of a medicament for treating primary and secondary hypogonadism in a male, said medicament is in a form intended for injectable administration and further comprises a vehicle comprising castor oil and a co-solvent.

The present inventors provide herein evidence for that upon applying a first injection interval of 6 weeks (injection of a first dose followed by a second dose 6 weeks after the first injection), the time until steady-state conditions is shortened. Thus, a maintenance phase may start already after 6 weeks of therapy. As further shown herein, the subsequent injection of testosterone undecanoate can be conducted using intervals of 10 weeks or 12 weeks between injections so as to achieve serum testosterone levels remaining well within the normal range of 10 to 35 nmol/l throughout the entire period between injections. Thus, an injection scheme resulting in reliable serum testosterone levels ranging from 10-35 nmol/L has been found.

The pharmacokinetic profile of the composition of the invention allows for extended periods between injections when steady state conditions is first achieved. Thus, in preferred embodiments of the invention, the maintenance phase comprises that the subsequent injections are conducted with an interval of 10 weeks between subsequent injections, preferably with an interval of 11 weeks, such as intervals of 12, 13, 14, 15 and 16 weeks between subsequent injections of the compositions of the invention.

The actual dose of testosterone ester being injected will also modify the depot effect of the compositions of the invention. Therefore, in suitable embodiments of the invention, the injected single dose of said testosterone ester is in an amount therapeutically equivalent to a single dose of testosterone undecanoate of between 750 to 1500 mg. Preferably, 1000 mg of testosterone undecanoate is injected as a single dose or any therapeutically equivalent dose of another testosterone undecanoate of the invention.

As may be understood, the single doses referred to above, such as the doses injected during the initial phase and the doses injected during the maintenance phase may be similar or different. Therefore, in some embodiments of the invention, the doses injected during the initial phase comprise the same amount of testosterone ester. In other embodiments, the doses injected during the initial phase are different from one injection to another. Similarly, in some embodiments, the doses injected during the maintenance phase are similar throughout the period or they may vary. Obviously, the doses applied in the initial phase may differ from those applied in the maintenance phase. However, preferably the doses of the testosterone esters injected in the initial phase and maintenance phase comprises the same amount of testosterone ester.

As mentioned above, the invention relates to a method of treating diseases and symptoms associated with deficient endogenous levels of testosterone in a male, such as a mammalian male, such as a man. As used herein, deficient levels of testosterone in a man, such as a hypogonadal man, is meant to encompass levels testosterone in serum less than 10 or 9 nmol/l.

In one embodiment of the invention, the deficient endogenous levels of testosterone may be caused by therapy with progestins or gonadotropin suppressive agents. Thus, methods of treating deficient endogenous levels of testosterone in a male may imply methods for male contraception. Therefore, in some embodiments of the invention, methods of treatment and uses are directed to male contraception, optionally wherein a progestin or a further gonadotropin suppressive agent is included in the treatment.

Hence, in still further aspects, the invention relates to the use of a of a testosterone ester selected from the group of esters consisting of linear and branched C-9 to C-16 alkanoates for the preparation of a medicament for treating diseases and symptoms associated with deficient levels of testosterone in a male in therapy with a progestin or a further gonadotropin suppressive agent, said medicament is in a form intended for being injected, such as in a form for intramuscular injection, and the testosterone ester, such as testosterone undecanoate is in a vehicle comprising castor oil and a co-solvent.

In general, the invention relates to the use of a composition as defined herein for male contraception or for treating diseases and symptoms associated with deficient endogenous levels of testosterone in a male.

Generally speaking, diseases and symptoms of deficient endogenous levels of testosterone in a male may imply sexual dysfunction, reduced muscle mass and muscle strength, depressed mood and/or osteoporosis.

Diseases of interest relate in general to primary and secondary hypogonadism and hypophyseal diseases. Thus, embodiments of the invention include treatment of diseases associated with primary and secondary hypogonadism and hypophyseal diseases. Primary hypogonadism may be derived from testicular failure such as resulting from cryptorchidism, bilateral testicular torsion, orchitis, orchidectomy, Klinefelter syndrome, chemotherapy and toxic damage from alcohol or heavy metals. Secondary hypogonadism may be derived from idiopathic gonadotropin releasing hormone (GnRH) deficiency or pituitary-hypothalamic injury associated with tumours, trauma or radiation.

Hence, in some embodiments of the invention, the treatment and uses of the invention is directed to a hypogonadal man, a man with hypophyseal diseases and/or a man in therapy with gonadotropin-suppressive agents or progestins.

Furthermore, as stated the single dose of a testosterone ester need to be justified so as to achieve reliable serum testosterone levels. Thus, in some embodiments, said use of a testosterone ester for the preparation of a medicament comprises that said testosterone ester is in a unit dose therapeutically equivalent to a dose of testosterone undecanoate, or that said testosterone ester is in a dose, corresponding to a 6-week dose of 500 mg to 2000 mg of testosterone undecanoate. In some embodiments, the dose corresponds to a 9-week dose of 500 mg to 2000 mg of testosterone undecanoate, a 10-week dose of 500 mg to 2000 mg, a 11-week dose of 500 mg to 2000 mg, a 12-week dose of 500 mg to 2000 mg, a 13-week dose of 500 mg to 2000 mg, a 14-week dose of 500 to 2000 mg, a 15-week dose of 500 to 2000 mg and a 16-week dose of 500 mg to 2000 mg. Preferably, such 6-, 9-, 10-, 11-, 12-, 13-, 14-, 15- and 16-week doses of a testosterone ester are therapeutically equivalent to a dose of testosterone undecanoate of 750 mg to 1500 mg, preferably of 1000 mg.

As may be further understood, the method of treatments and uses as described herein include embodiments wherein the testosterone ester, such as testosterone undecanoate is provided in a composition as defined herein.

FIGURES

FIG. 1. Total levels of testosterone in serum following injection of testosterone undecanoate.

The FIGURE shows the levels of testosterone (total amounts) following injecting a formulation of testosterone undecanoate in a vehicle containing 4 ml of a mixture of castor oil and benzyl benzoate in a ratio of 1:1.7 by volume. See Example 3 for the injection scheme. The dotted lines shows the initial phase of two injections of 1000 mg of TU with an interval of 6 weeks, followed by 3 injections of TU with an interval of 10 weeks between injections. The filled lines show the continued injection of 1000-mg TU with an interval of 12 weeks between injections.

EXAMPLES

Example 1

Compositions According to the Present Invention are Formulated for Intramuscular Injection and Prepared According to Techniques Known by a Person Skilled in the Art Compositions are in general prepared by incorporating a therapeutically effective amount of any of testosterone ester of the invention, such as the testosterone undecanoate, in an appropriate vehicle comprising castor oil and a co-solvent, such as benzyl benzoate. Further excipients may be added. Finally, the compositions are subjected to a sterilisation process. The vehicle wherein the active substance is dissolved may comprise excipients such as preservatives, stabilising agents, co-solvents and antioxidants. Suitable vehicles are sterile, pyrogen-free and free of particles.

The compositions may be presented in unit dosage form, e.g., in ampoules or in multi-dose containers.

The preparation of compositions according to one embodiment of the invention may comprise the following steps:
i) Pre sterilisation of excipients and testosterone esters.
ii) Preparation of a solution of testosterone esters
iii) Addition of one or more excipients to the solution of testosterone esters
iv) Filtration of the composition
v) Preparation/filling of single or multi-dose containers
vi) Sterilisation.

In one specific example of the invention the testosterone undecanoate is dissolved in benzyl benzoate, the testosterone undecanoate/co-solvent solution is then combined with the castor oil, which is then filtrated through a 0.2 µm filter, filled into amber-glass bottles, and finally sterilised at 180° C. for 3 hours.

Example 2

The therapeutic efficacy and safety of a formulation containing testosterone undecanoate 1000 mg in a vehicle of 4 ml of a mixture of castor oil and benzyl benzoate in a ratio of 1:1.7 by volume has been investigated in hypogonadal men. The formulation (4 mL, 1000 mg of testosterone undecanoate) was injected intramuscularly to the hypogonadal men according to the following scheme:
   initial phase comprising 4 injections of the formulation with intervals of 6 weeks between the injections.
   maintenance phase comprising injecting the formulation in intervals of 10 or 12 weeks between injections.

The present study relates to a one-arm study examining the efficacy and safety of long-term intramuscular injection of testosterone undecanoate for the treatment of symptoms of hypogonadism in men. The patients received 4 testosterone undecanoate injections of 1000 mg the first three times of injections with an interval of 6 weeks, the 4$^{th}$ injection and subsequent injections with 12-week intervals.
Protocol:

| | |
|---|---|
| Name of active ingredient: | Testosterone Undecanoate (TU) |
| Objectives: | To obtain further information on efficacy and safety of the TU preparation after long-term administration over a period of more than 18 months at prolonged (12-week) intervals between the injections of 1000 mg TU in 4 ml oily solution |
| Methodology: | Open, one-arm, multiple-dose study |
| Total number of subjects: | planned: 36 |
| Diagnosis and main criteria for inclusion: | Hypogonadal men aged 18 to 65 years and with serum T (testosterone) levels without androgen treatment lower than 5 nmol/L, who orderly completed the main study with a final examination, did not exhibit any relevant pathological findings, and gave their written informed consent to either extend the TU treatment from the main study or switch over from TE (testosterone enanthate) to TU |
| Test product: | Testosterone Undecanoate (TU) |
| dose: | in patients on TU: 8 × 1000 mg at 12-week intervals |
| mode of administration: | Intramuscular injections (gluteus medius muscle) |
| Duration of treatment: | 80 weeks 84 weeks |
| Efficacy end points: | Primary variables: erythropoiesis (hemoglobin, hematocrit), grip strength; Secondary variables: serum levels of testosterone (T), dihydrotestosterone (DHT), estradiol (E2), luteinizing hormone (LH), follicle stimulating hormone (FSH), leptin and sex hormone-binding globulin (SHBG); bone density; parameters of bone metabolism; body composition; lipids (total cholesterol, triglycerides, low-density, high-density and very low-density lipoproteins, apolipoprotein A1 and B, lipoprotein (a)) |
| Safety end points: | Adverse events (AEs); serum level of prostate-specific antigen (PSA); ultrasonographic findings in prostate; hematological and liver (ASAT, ALAT, gamma-GT, total bilirubin) parameters, ferritin, iron; |

The results of this study allow for the following conclusion:

Treatment with only 4 TU doses of 1000 mg i.m. per year was sufficient to restore physiological serum T levels in all 36 patients over most of the measurement times. This demonstrates that an injection interval of 12 weeks is adequate for most of the patients.

Example 3

Pharmacokinetic Profile of Compositions of the Invention

The pharmacokinetic profile of a formulation containing testosterone undecanoate (TU) 1000 mg in a vehicle of 4 ml of a mixture of castor oil and benzyl benzoate in a ratio of 1:1.7 by volume was tested in hypogonadal men (having testosterone levels in serum of less than 10 nmol/l). An initial phase of two first intramuscularly injections of 1000 mg TU with 6-weeks interval between the two injections, followed by a maintenance phase of subsequent 3 intramuscularly injections of 1000 mg TU separated by an interval of 10 weeks between each of the injections. Then 1000 mg of testosterone undecanoate (TU) was intramuscularly injected every 12 weeks. 5 treatment periods were provided with an interval of 12 weeks between each injection.

The result from this study shows (see FIG. 1) that the treatment scheme resulted in testosterone levels (total levels) wherein the maximal and minimal levels are within the physiological acceptable range and no accumulation of testosterone is seen over time. Furthermore, the minimum testosterone levels (total levels) after 12 weeks do not fall below the lowest acceptable concentration of testosterone of about 10 nmol. The same was shown to apply for a treatment period of 14 weeks upon extrapolating the serum levels of testosterone. The study also demonstrated that injection of 1000 mg of TU in the above-mentioned formulation in intervals of 12 weeks between injections was efficient over a period of 14 weeks.

Example 4

Comparison of Initial Phases with 6 Weeks Between Injections and 10 Weeks Between Injections The pharmacokinetic profile of a formulation containing testosterone undecanoate (TU) 1000 mg in a vehicle of 4 ml of a mixture of castor oil and benzyl benzoate in a ratio of 1:1.7 by volume was tested using two different regimens in hypogonadal men.

In regimen A, an initial phase of two first intramuscularly injections of 1000 mg TU with mean of 9.2-weeks (64.4 days) interval between the two injections, followed by a maintenance phase of subsequent intramuscularly injections of 1000 mg TU separated by an interval of a mean of 10.2 weeks (76.2 days) after second injection.

In regimen B, an initial phase of two first intramuscularly injections of 1000 mg TU with mean of 6.1-weeks (42.5 days) interval between the first two injections, followed by a maintenance phase of subsequent intramuscularly injections of 1000 mg TU separated by an interval of mean of 10.1 weeks (70.5 days) after second injections.

The concentration of testosterone (total) was determined in serum before each additional injection of TU.

Results.

The table below shows the mean serum levels of testosterone (total) for regimen A versus regimen A based on data for 6 men.

Mean Testosterone Levels (Total) in Serum According to the Number of Weeks Between Injections.

| Regime | Base value; mean testosterone level (nmol/l) before 1$^{st}$ injection | 1$^{st}$ injection Mean weeks after 1$^{st}$ injection | Mean testosterone level (nmol/l) after weeks | 2$^{nd}$ injection Mean weeks after 2$^{nd}$ injection | Mean testosterone level (nmol/l) after weeks |
|---|---|---|---|---|---|
| A | 7.9 | 9.2 | 7.0 | 10.8 | 8.8 |
| B | 6.8 | 6.1 | 12.2 | 10.1 | 12.5 |

It appears that regimens including long-term intervals between injections, both with respect to the initial phase and maintenance phase, do not result in the sufficient levels of testosterone above 10 nmol over the entire period and up to the following injection (Regimen A). However, upon decreasing the interval between injections in the initial phase to 6 weeks, a reliable regimen is achieved, wherein sufficient testosterone levels are reinstated very fast and remains at levels above 10 nmol/l.

We claim:

1. A method of providing prolonged physiologically acceptable steady state serum testosterone levels in a patient deficient in endogenous testosterone levels comprising intramuscularly administering a maintenance dose of a composition comprising testosterone undecanoate and a vehicle consisting essentially of castor oil and a co-solvent, wherein the castor oil is present in the vehicle in a concentration of 42 percent or less by volume, once every 10-14 weeks following 2-4 initial doses of said composition, each initial dose being administered at an interval of 4-8 weeks.

2. The method of claim 1, which is for treating primary or secondary hypogonadism in a man.

3. The method of claim 2, wherein primary hypogonadism is treated and said primary hypogonadism is derived from: testicular failure due to cryptorchidism, bilateral testicular torsion, orchitis, orchidectomy, Klinefelter syndrome, chemotherapy or toxic damage from alcohol or heavy metals.

4. The method of claim 2, wherein secondary hypogonadism is treated and said secondary hypogonadism is caused by idiopathic gonadotropin releasing hormone (GnRH) deficiency or pituitary-hypothalamic injury from tumours, trauma or radiation.

5. The method of claim 1, which is for treating a disease or symptom associated with a deficient level of testosterone in a man who is in therapy with a progestin or a gonadotropin suppressive agent.

6. The method according to claim 1, in which 2 initial doses are administered at an interval of 4 weeks between injections, followed by the maintenance dose once every 10-14 weeks.

7. The method of claim 6, in which the maintenance dose is administered once every 10 weeks.

8. The method according to claim 1, in which 2 initial doses are administered at an interval of 6 weeks between injections, followed by the maintenance dose once every 10-14 weeks.

9. The method of claim 8, in which the maintenance dose is administered once every 12 weeks.

10. The method according to claim 1, in which the co-solvent is benzyl benzoate.

11. The method of claim 10, wherein castor oil and benzyl benzoate are in a ratio of from 1:1 to 1:1.6 (v/v).

12. The method according to claim 1, which provides steady state serum testosterone levels ranging from about 10 nmol/L to about 35 nmol/L.

13. The method according to claim 1, in which each dose contains 750 mg of testosterone undecanoate.

14. A method of treating a disease or symptom associated with deficient endogenous levels of testosterone in a man, comprising administering by intramuscular injection a composition comprising testosterone undecanoate (TU) and a vehicle consisting essentially of castor oil and a co-solvent, the castor oil being present in the vehicle at a concentration of 42 percent or less by volume, the method further comprising:
   (i) an initial phase comprising 2 initial intramuscular injections of a dose of TU at an interval of 4 weeks between injections, each dose including 500 mg to 1000 mg of TU, followed by,
   (ii) a maintenance phase comprising subsequent intramuscular injections of a dose of TU at an interval of 10 weeks between injections, each dose including 500 mg to 1000 mg of TU.

15. The method of claim 14, in which the castor oil is present in the vehicle in a concentration ranging from 25 to 42 percent by volume.

16. The method of claim 14, in which the co-solvent is benzyl benzoate.

17. The method of claim 16, in which the benzyl benzoate is present in the vehicle in a concentration ranging from 58 to 75 percent by volume.

18. The method of claim 14, in which each dose contains 750 mg of TU.

19. The method according to claim 14, wherein the man is a hypogonadal man, a man with a hypophyseal disease or a man in therapy with a gonadotropin-suppressive agent or progestin.

20. The method according to claim 14, wherein said disease or symptom is associated with primary or secondary hypogonadism or a hypophyseal disease.

21. The method according to claim 20, wherein said disease or symptom is associated with primary hypogonadism which is derived from testicular failure due to cryptorchidism, bilateral testicular torsion, orchitis, orchidectomy, Klinefelter syndrome, chemotherapy or toxic damage from alcohol or heavy metals.

22. The method according to claim 20, wherein said disease or symptom is associated with secondary hypogonadism caused by idiopathic gonadotropin releasing hormone (GnRH) deficiency or pituitary-hypothalamic injury from tumours, trauma or radiation.

23. The method according to claim 14, further comprising administering a progestin or a further gonadotropin suppressive agent.

24. A method for male contraception in a man comprising intramuscularly administering to the man a maintenance dose of a composition comprising testosterone undecanoate and a vehicle consisting essentially of castor oil and a co-solvent, wherein the castor oil is present in the vehicle in a concentration of 42 percent or less by volume, once every 10-14 weeks following 2-4 initial doses of said composition, each initial dose being administered at an interval of 4-8 weeks.

25. The method of claim 1, in which each dose contains 250 mg/ml of testosterone undecanoate.

26. The method of claim 14, in which each dose contains 250 mg/ml of testosterone undecanoate.

27. The method of claim 14, in which each dose contains 250 mg/ml of testosterone undecanoate.

* * * * *

UNITED STATES PATENT AND TRADEMARK OFFICE

(12)  CERTIFICATE EXTENDING PATENT TERM
UNDER 35 U.S.C. § 156

| | | | |
|---|---|---|---|
| (68) | PATENT NO. | : | 8,338,395 |
| (45) | ISSUED | : | December 25, 2012 |
| (75) | INVENTOR | : | Doris Hubler et al. |
| (73) | PATENT OWNER | : | Bayer Intellectual Property GmbH |
| (95) | PRODUCT | : | AVEED® (testosterone undecanoate) |

This is to certify that an application under 35 U.S.C. § 156 has been filed in the United States Patent and Trademark Office, requesting extension of the term of U.S. Patent No. 8,338,395 based upon the regulatory review of the product AVEED® (testosterone undecanoate) by the Food and Drug Administration. According to United States Patent and Trademark Office records, the original expiration date of the patent as of the date of issuance of this certificate is February 27, 2026. Because it appears that the requirements of the law have been met, this certificate extends the term of the patent for the period of

(94) 435 days subject to the payment of maintenance fees as provided by law, with all rights pertaining thereto as provided by 35 U.S.C. § 156.

I have caused the seal of the United States Patent and Trademark Office to be affixed this 19th day of August 2020.

Andrei Iancu
Under Secretary of Commerce for Intellectual Property and
  Director of the United States Patent and Trademark Office